US007264774B1

(12) United States Patent
Howard

(10) Patent No.: US 7,264,774 B1
(45) Date of Patent: Sep. 4, 2007

(54) METHOD AND APPARATUS FOR SANITIZING A DRAIN

(76) Inventor: David Howard, 3045 S. Trenton, Tulsa, OK (US) 74114

( * ) Notice: Subject to any disclaimer, the term of this patent is extended or adjusted under 35 U.S.C. 154(b) by 390 days.

(21) Appl. No.: 11/085,353

(22) Filed: Mar. 21, 2005

(51) Int. Cl.
*A61L 2/18* (2006.01)
*E03D 9/00* (2006.01)

(52) U.S. Cl. .............................. 422/28; 4/222; 138/93
(58) Field of Classification Search ............... None
See application file for complete search history.

(56) References Cited

U.S. PATENT DOCUMENTS 2,311,197 A * 2/1943 Ahern ..................... 134/24

FOREIGN PATENT DOCUMENTS

JP 7279206 A * 10/1995

* cited by examiner

*Primary Examiner*—E. Leigh McKane
(74) *Attorney, Agent, or Firm*—Fellers, Snider, Blankenship, Bailey & Tippens, P.C.; Dennis D. Brown

(57) ABSTRACT

A method of sanitizing a drain having a drain conduit with a drain trap therein and an improved floor drain for use in the method of sanitizing. The method comprises the steps of (a) temporarily blocking the drain conduit at a position downstream of the trap and (b) at least partially back-filling the drain upstream of the blocked position with a sanitizing fluid.

18 Claims, 1 Drawing Sheet

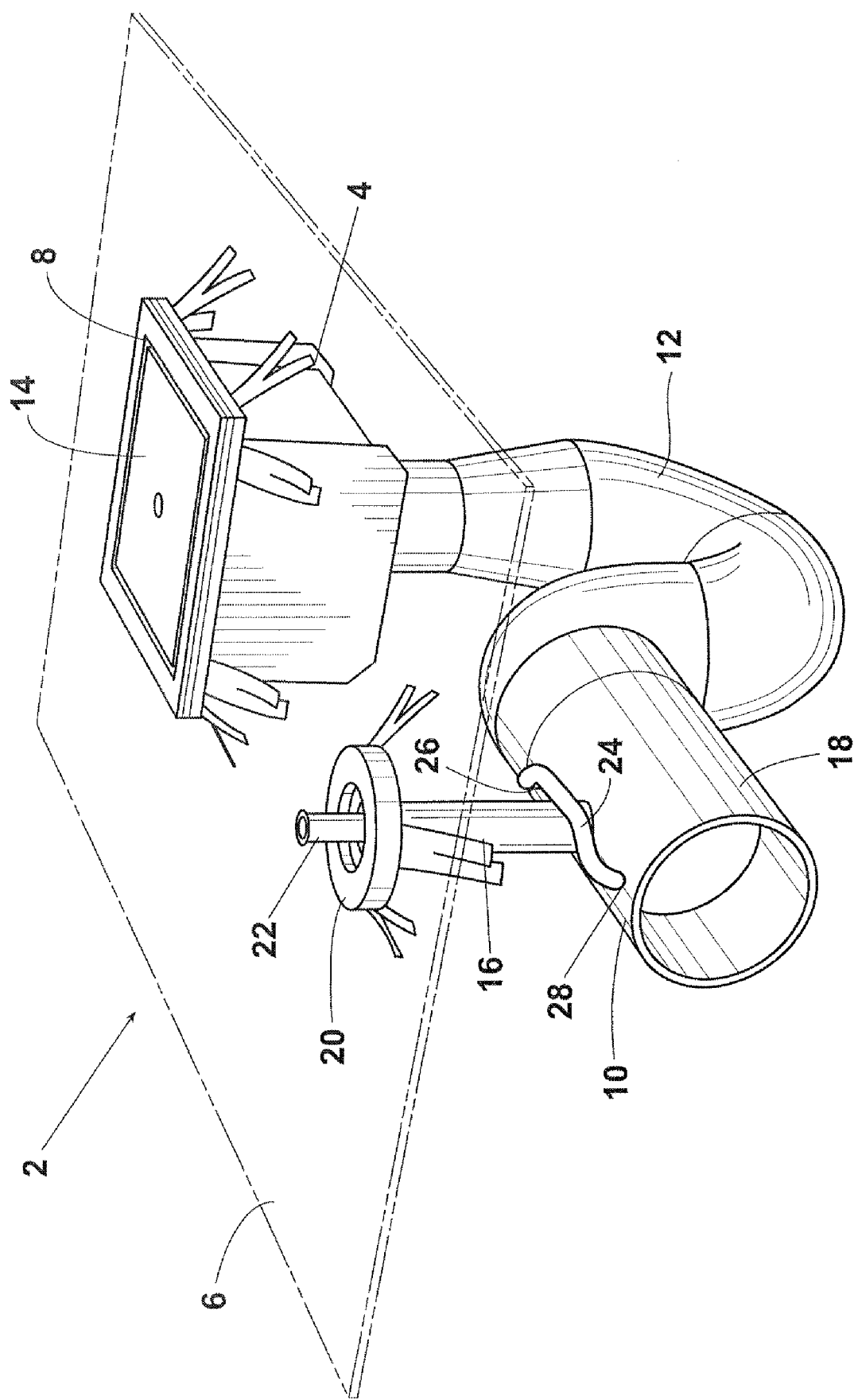

METHOD AND APPARATUS FOR SANITIZING A DRAIN

FIELD OF THE INVENTION

The present invention relates to methods and apparatuses for sanitizing drains. More particularly, but not by way of limitation, the present invention relates to methods and apparatuses for sanitizing floor drains and other drainage systems having drain traps therein.

BACKGROUND OF THE INVENTION

Floor drain assemblies are commonly used in the food industry for draining condensation, spills, cleaning solutions, and other fluids from the floors of food processing plants. A typical floor drain assembly comprises: a drain box or other receiving structure which is installed in the floor and has an upper opening substantially at floor level for receiving floor drainage; a sub-floor drain conduit extending from the receiving structure for delivering the drainage material to a sewer or waste water treatment system; and a downwardly extending, sub-floor drain trap (such as, e.g., a curved downwardly extending P-trap) provided in the drain conduit. The trap is configured such that a sufficient liquid level is maintained in the lower curved portion of the trap to prevent odors and gases from backflowing through the drain into the plant environment.

It is now recognized in the industry that *Listeria monocytogenes* and other pathogens can be particularly prevalent on the floors and in the floor drain systems of food processing plants. Unfortunately, although hundreds of gallons of floor sanitizing solutions can be flushed down the floor drains of a food processing plant as a matter of daily practice, the floor drain assemblies are typically configured such that that the sanitizing solutions are unable to reach and sanitize all of the internal surfaces of the drain. This is particularly so in the case of drain assemblies which include P-traps or other downwardly extending drain trap structures beneath the floor surface. Thus, a need exists for an effective method and apparatus for sanitizing the sub-floor pipe work of the floor drain assemblies used in food processing plants and other facilities.

SUMMARY OF THE INVENTION

The present invention satisfies the needs and alleviates the problems discussed above. The present invention is well suited for use in floor drains, sink drains, and other types of drain assemblies and is particularly desirable for use in drain assemblies having P-traps or other drain trap structures.

In one aspect, there is provided a method of sanitizing a drain having a drain conduit with a drain trap therein comprising the steps of: (a) temporarily blocking the drain conduit at a position downstream of the drain trap; (b) at least partially back-filling the drain upstream of the position with a sanitizing fluid; and (c) during step (b), venting air from the drain conduit upstream of the position to a location of the drain conduit downstream of the position. As used herein, the term "sanitizing fluid" refers to any type of sanitizing solution or other sanitizing liquid material.

In another aspect, there is provided a method of sanitizing a drain having a drain conduit with a drain trap therein comprising the steps of: (a) inflating an inflatable device in the drain conduit downstream of the drain trap; (b) at least partially back-filling the drain upstream of the inflatable device with a sanitizing fluid; and (c) deflating the inflatable device.

In another aspect, there is provided an improvement for a floor drain having a drainage receiving structure installable in the floor, a drain conduit extending from the drainage receiving structure for installation beneath the floor, and a drain trap in the drain conduit. The improvement comprises an insertion conduit extending upwardly from the drain conduit downstream of the drain trap for inserting a blocking device into the drain conduit for temporarily blocking the drain conduit downstream of the drain trap. The insertion conduit has an upper end installable in the floor. The improvement also preferably further comprises a venting line for venting air around the blocking device, the venting line having a vent inlet end connected to the drain conduit upstream of the insertion conduit and a vent outlet end connected to the drain conduit downstream of the insertion conduit.

Further aspects, features and advantages of the present invention will be apparent to those in the art upon examining the accompanying drawing and upon reading the following detailed description of the preferred embodiments.

BRIEF DESCRIPTION OF THE DRAWING

The drawing is a perspective view of an embodiment 2 of the inventive floor drain assembly.

DETAILED DESCRIPTION OF THE PREFERRED EMBODIMENTS

An embodiment 2 of the improved floor drain assembly is depicted in the drawing. The floor drain assembly comprises: a drain box or other receiving structure 4 for installation in a floor 6 such that the top 8 of the drain box 4 is substantially flush with the floor 6; a drainpipe or other drain conduit 10 extending beneath the floor 6 from the bottom of the drain box 4 to a sewer or wastewater treatment system (not shown) and; a P-trap or other drain trap structure 12 provided in the drain conduit 10. The drain box 4 can include a removable cover 14 and can also include an internal removable cage or other straining device (not shown).

In accordance with the present invention, the improved floor drain assembly 2 also preferably comprises: an insertion pipe or other conduit 16 extending upwardly from the top of a substantially horizontal or slightly downwardly sloped portion 18 of the drain conduit 10 downstream of the trap 12; an inlet flange 20 installed in the floor 6 on the upper end of the insertion pipe 16; a blocking device (preferably an inflatable device) 22 extending through the insertion pipe 16 into the drain conduit 10 for temporarily blocking the drain conduit 10 downstream of the trap 12; and a vent bypass line 24 installed on the top of the downstream portion 18 of the drain conduit 10 around the insertion pipe 16 and around the blocking device 22. The vent bypass line 24 has an inlet end 26 connected to the drain conduit 10 at a location upstream of the insertion pipe 16 and an outlet end 28 connected to the drain conduit 10 at a location downstream of the insertion pipe 16.

As indicated above, the blocking device 22 employed in the inventive drain assembly will preferably be an inflatable blocking device. The inflatable blocking device 22 can be an inflatable bladder, an inflatable balloon, or any other inflatable device capable of affectively blocking the drain conduit 10 for cleaning. The inflatable device 22 can be either permanently or removably inserted through the insertion pipe 16 and will most preferably be removably insertable therethrough. The inlet flange 20 of the insertion pipe 16 will preferably be adapted for receiving a plug, cover, or other structure for closing the upper end of the insertion pipe 16 when not in use.

The inventive sanitizing method can be used for sanitizing generally any type of drain assembly. The inventive sanitizing method is particularly well suited for use in conjunction with the inventive floor drain assembly 2 depicted in the drawing but is also well suited for use in sanitizing generally any other type of drain assembly which utilizes a drain trap structure.

In accordance with the inventive drain sanitizing method, the drain conduit 10 is preferably first temporarily blocked at a position downstream of the drain trap 12. Although other devices can be used, this step is preferably accomplished by inflating an inflatable device 22 such as an inflatable bladder or an inflatable balloon in the drain conduit 10 downstream of the trap 12. The inflatable device 22 is preferably removably inserted into the drain conduit 10 via an upwardly extending insertion conduit 16.

The drain is preferably then at least partially back-filled upstream of the blocking device 22 with an amount of sanitizing fluid effective for contacting and sanitizing the interior surfaces of the drain assembly 2 in and around the trap 12. The back-filling of the drain assembly 2 is preferably accomplished by pouring the sanitizing fluid into the drain box 4.

During the back-filling step of the inventive process, the air trapped within the drain conduit 10 upstream of the blocking device 22 is vented around the blocking device 22 and into the downstream portion of the drain conduit 10 via the vent bypass line 24. The air is thus prevented from backflowing through the drain and thereby carrying airborne pathogens into the plant environment. The vent bypass line 24 is preferably located on top of the substantially horizontal or slightly sloped downstream portion 18 of the drain conduit 10 such that, after substantially all of the trapped air in the upstream portion of the drainpipe has been vented through the vent bypass line 24, the vent bypass line 24 itself will then be filled with and sanitized by the sanitizing fluid.

Upon completion of the back-filling step, the drain conduit 10 is unblocked so that the sanitizing fluid is allowed to flow through the drain conduit 10 to the sewer or waste treatment system. If an inflatable device such as a bladder or balloon 22 is used for temporarily blocking the drain conduit 10, the drain conduit 10 can be unblocked by simply deflating the device 22. If a removable blocking device 22 is employed, the device is also preferably removed from the insertion pipe 16 and appropriately treated with the sanitizing fluid. The upper opening of the insertion pipe 16 is then closed.

Thus, the present invention is well adapted to carry out the objects and attain the ends and advantages mentioned above as well as those inherent therein. While presently preferred embodiments have been described for purposes of this disclosure, numerous changes and modifications will be apparent to those skilled in the art. Such changes and modifications are encompassed within the spirit of this invention as defined by the appended claims.

What is claimed is:

1. A method of sanitizing a drain having a drain conduit with a drain trap therein comprising the steps of:
    (a) temporarily blocking said drain conduit at a position downstream of said drain trap;
    (b) at least partially back-filling said drain upstream of said position with a sanitizing fluid; and
    (c) during step (b), venting air from said drain conduit upstream of said position to a location of said drain conduit downstream of said position.

2. The method of claim 1 wherein said drain conduit is temporarily blocked in step (a) by inflating an inflatable device in said drain conduit at said position.

3. The method of claim 2 wherein said inflatable device is an inflatable bladder or an inflatable balloon.

4. The method of claim 2 further comprising the step, following step (b), of (d) unblocking said drain conduit at said position by deflating said inflatable device.

5. The method of claim 2 wherein said inflatable device extends into said drain conduit through an insertion conduit extending from said drain conduit.

6. The method of claim 1 wherein said air is vented in step (c) through a venting line extending from a location of said drain conduit upstream of said position to said location of said drain conduit downstream of said position.

7. The method of claim 6 wherein said venting line is positioned such that said venting line is flooded with said sanitizing fluid in step (b) after substantially all of said air is vented in step (c) from said drain conduit upstream of said position.

8. The method of claim 1 wherein said trap is a P-trap.

9. A method of sanitizing a drain having a drain conduit with a drain trap therein comprising the steps of:
    (a) inflating an inflatable device in said drain conduit downstream of said drain trap;
    (b) at least partially back-filling said drain upstream of said inflatable device with a sanitizing fluid; and
    (c) deflating said inflatable device;
    wherein said method further comprises the step, during step (b) of venting air from said drain conduit upstream of said inflatable device to a location of said drain conduit downstream of said inflatable device.

10. The method of claim 9 wherein said inflatable device is an inflatable bladder or an inflatable balloon.

11. The method of claim 9 further comprising the step, prior to step (a), of inserting said inflatable device into said drain conduit.

12. The method of claim 11 wherein:
    said drain conduit and said drain trap are located beneath a floor and
    said inflatable device is inserted into said drain conduit in said step of inserting through a conduit extending from said floor to said drain conduit.

13. The method of claim 11 further comprising the step of (d) removing said inflatable device from said drain conduit.

14. The method of claim 9 wherein said air is vented in said step of venting through a venting line extending from a location of said drain conduit upstream of said inflatable device to said location of said drain conduit downstream of said inflatable device.

15. The method of claim 14 wherein said venting line is positioned such that said venting line is flooded with said sanitizing fluid in step (b) after substantially all of said air is vented in said step of venting from said drain conduit upstream of said inflatable device.

16. The method of claim 9 wherein said trap is a P-trap.

17. In a floor drain having a drainage receiving structure installable in a floor, a drain conduit extending from said drainage receiving structure for installation beneath said floor, and a drain trap in said drain conduit, the improvement comprising an insertion conduit extending upwardly from said drain conduit downstream of said drain trap for inserting a blocking device into said drain conduit for temporarily blocking said drain conduit downstream of said drain trap, said insertion conduit having an upper end installable in said floor and the improvement further comprising a venting line for venting air around said blocking device, said venting line having a vent inlet end connected to said drain conduit upstream of said insertion conduit and a vent outlet end connected to said drain conduit downstream of said insertion conduit.

18. The floor drain of claim 17 wherein the improvement further comprises a flange on said upper end of said insertion conduit for installation in said floor.

* * * * *